United States Patent
Irakoze et al.

(10) Patent No.: US 11,589,174 B2
(45) Date of Patent: Feb. 21, 2023

(54) COCHLEAR IMPLANT SYSTEMS AND METHODS

(71) Applicants: Arizona Board of Regents on Behalf of Arizona State University, Scottsdale, AZ (US); Aymard Irakoze, Scottsdale, AZ (US); Brian Lambert, Scottsdale, AZ (US); Matthew Edick, Scottsdale, AZ (US); J. Nathan Gross, Scottsdale, AZ (US); Noel Robles, Scottsdale, AZ (US)

(72) Inventors: Aymard Irakoze, Phoenix, AZ (US); Brian Lambert, Gilbert, AZ (US); Matthew Edick, Tempe, AZ (US); J. Nathan Gross, Wildwood, MO (US); Noel Robles, Tempe, AZ (US); Jitendran Muthuswamy, Chandler, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 200 days.

(21) Appl. No.: 17/113,638

(22) Filed: Dec. 7, 2020

(65) Prior Publication Data
US 2021/0170172 A1 Jun. 10, 2021

Related U.S. Application Data

(60) Provisional application No. 63/019,146, filed on May 1, 2020, provisional application No. 62/945,002, filed on Dec. 6, 2019.

(51) Int. Cl.
*A61N 1/36* (2006.01)
*H04R 25/00* (2006.01)

(52) U.S. Cl.
CPC .......... *H04R 25/507* (2013.01); *H04R 25/30* (2013.01); *H04R 25/70* (2013.01); *A61N 1/36038* (2017.08); *H04R 2225/67* (2013.01)

(58) Field of Classification Search
CPC .................................................. H04R 25/507
See application file for complete search history.

(56) References Cited

U.S. PATENT DOCUMENTS

2008/0240458 A1* 10/2008 Goldstein ............ H04R 1/1083
381/72
2012/0224707 A1* 9/2012 Kim ....................... H04L 67/52
381/56

(Continued)

OTHER PUBLICATIONS

Afshine Amidi, & Shervine Amidi. (n.d.). CS 230—Recurrent Neural Networks Cheatsheet. Stanford.Edu. Retrieved Apr. 22, 2020, from https://stanford.edu/~shervine/teaching/cs-230/cheatsheet-recurrent-neural-networks.

(Continued)

*Primary Examiner* — Mark Fischer
(74) *Attorney, Agent, or Firm* — Snell & Wilmer L.L.P.

(57) ABSTRACT

Systems and methods for improved control and performance of cochlear implants are disclosed. In an embodiment, the audio environment is sampled, and a neural network determines suggested filter setting for the cochlear implant. The process is repeated such that, as the user moves through various audio environments having differing noise levels, satisfactory performance of the cochlear implant is maintained for the user.

12 Claims, 8 Drawing Sheets

(56) References Cited

U.S. PATENT DOCUMENTS

| | | | | |
|---|---|---|---|---|
| 2015/0172831 A1* | 6/2015 | Dittberner | .............. | H04R 25/70 381/314 |
| 2016/0309267 A1* | 10/2016 | Fitz | ...................... | H04R 25/505 |
| 2019/0069107 A1* | 2/2019 | Gandhi | ................ | H04R 25/305 |

OTHER PUBLICATIONS

Flovik, V. (Mar. 1, 2020). Machine learning for anomaly detection and condition monitoring. Medium. https://towardsdatascience.com/machine-learning-for-anomaly-detection-and-condition-monitoring-d4614e7de770.

Gonzalez, R. (2013). Better Than MFCC Audio Classification Features. In J. S. Jin, C. Xu, & M. Xu, The Era of Interactive Media (pp. 291-301). Springer New York. https://doi.org/10.1007/978-1-4614-3501-3_24.

Introducing TensorFlow Federated, (n.d.). Retrieved Apr. 22, 2020, from https://blog.tensorflow.org/2019/03/introducing-tensorflow-federated.html.

McMahan, H. B., Moore, E., Ramage, D., Hampson, S., & Arcas, B. A. y. (2017). Communication-Efficient Learning of Deep Networks from Decentralized Data. ArXiv:1602.05629 [Cs]. http://arxiv.org/abs/1602.05629.

Mishra, S. (May 21, 2017). Unsupervised Learning and Data Clustering. Medium. https://towardsdatascience.com/unsupervised-learning-and-data-clustering-eeecb78b422a.

* cited by examiner

```
▼ Class: Park

[ ] filename = 'park-london-243-7254-a.wav'
    print_prediction(filename,loaded_model)

⤶ The predicted class is: park airport:  0.0000000003017832372886861053343
             bus:  0.0000000045891783429582984293
           metro:  0.0000000504390491239028051495552
   metro_station:  0.0000002811978447256448447043151519
            park:  0.99246597290039062500000000000000
   public_square:  0.0015265457321342682617187500000
   shopping_mall:  0.00000000357307483240029143131
 street_pedestrian: 0.0001802919541602306067943757300
   street_traffic:  0.0059258523971476548706054687500
            tram:  0.00003458436185610480605559387211
```

Fig. 3

COCHLEAR IMPLANT SYSTEMS AND METHODS

CROSS-REFERENCE TO RELATED APPLICATIONS

This application is a non-provisional of, and claims priority to, U.S. Provisional Application No. 62/945,002 filed Dec. 6, 2019 and entitled "COCHLEAR IMPLANT SYSTEMS AND METHODS." This application is also a non-provisional of, and claims priority to, U.S. Provisional Application No. 63/019,146 filed May 1, 2020 and entitled "COCHLEAR IMPLANT SYSTEMS AND METHODS." The contents of each of the foregoing applications are hereby incorporated by reference (except for any subject matter disclaimers or disavowals, and except to the extent of any conflict with the disclosure of the present application, in which case the disclosure of the present application shall control).

TECHNICAL FIELD

The present disclosure relates to cochlear implants and, more particularly, to systems and methods for control thereof.

BACKGROUND

Prior cochlear implant systems, such as hardware, software, or control algorithms, have suffered from various deficiencies. Accordingly, improved systems and methods remain desirable.

SUMMARY

In various embodiments, cochlear implant systems and methods are disclosed. In an exemplary embodiment, a computer-based method for controlling a cochlear implant comprises sampling, by a mobile application operative on a mobile device, an audio environment around a user of the cochlear implant to obtain audio environment information; converting the audio environment information to a set of mel-frequency cepstral coefficients; processing, by a neural network, the set of mel-frequency cepstral coefficients to determine a level of matching against a set of pre-defined noise environments; based on the level of matching, selecting, by the mobile application, filter configuration information associated with the best match in the set of pre-defined noise environments; and transmitting, by the mobile application and over a wireless link to the cochlear implant, the filter configuration information.

The contents of this section are intended as a simplified introduction to the disclosure, and are not intended to be used to limit the scope of any claim.

BRIEF DESCRIPTION OF THE DRAWINGS

The subject matter of the present disclosure is particularly pointed out and distinctly claimed in the concluding portion of the specification. A more complete understanding of the present disclosure, however, may be obtained by referring to the detailed description and claims when considered in connection with the drawing figures, wherein like numerals denote like elements.

FIG. 3 illustrates operation of neural network components of an exemplary cochlear implant system in accordance with various embodiments;

DETAILED DESCRIPTION

Figure 1A:
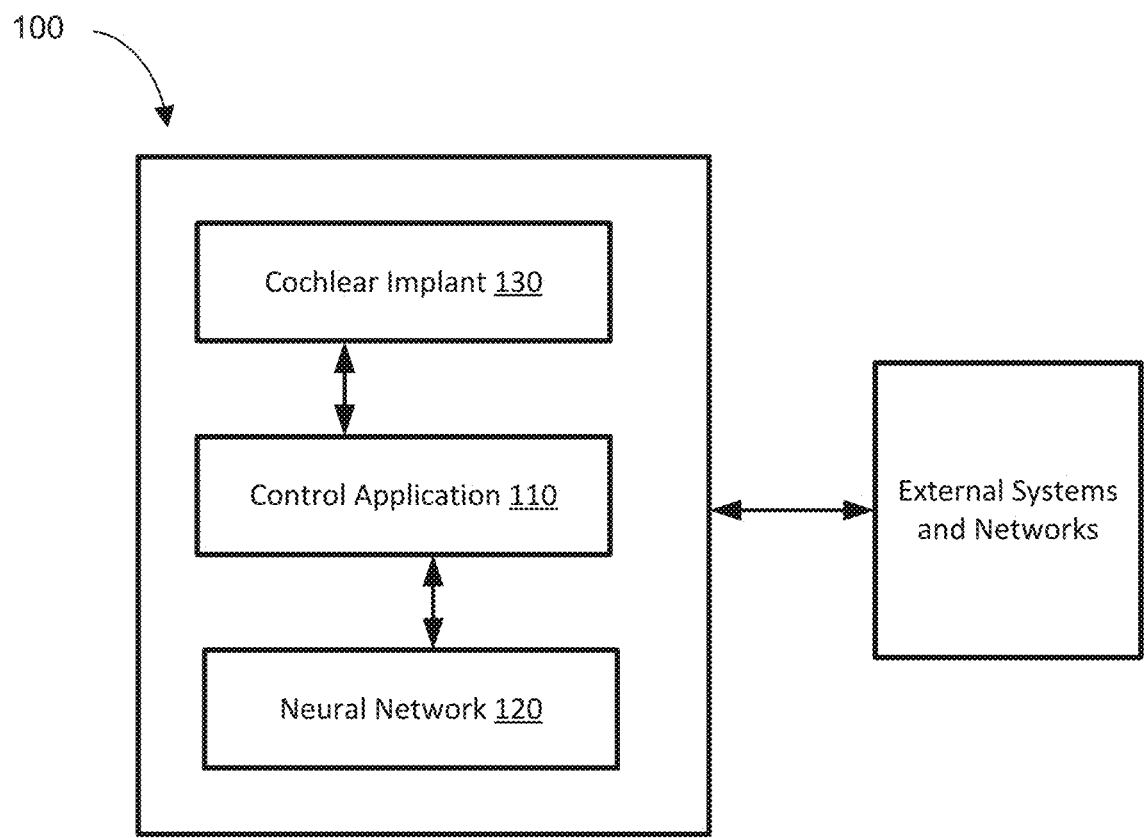
FIG. 1A is a block diagram illustrating an exemplary cochlear implant system, in accordance with various embodiments.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques for audio signal processing, wireless communications, neural network construction and/or training, machine learning, computer modeling, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical system, related methods, and/or products arising therefrom.

Patients who utilize cochlear implants often struggle with full control over their hearing. Often, the ambient "cocktail party" effect degrades the hearing quality of a patient, leading to patient dissatisfaction, miscommunication, and other undesirable outcomes. Prior cochlear implant systems, while offering various capabilities and potentially sophisticated hardware and software, do not address heating customization, for example in an intelligent and/or automated manner. Rather, with prior devices a patient typically must make an appointment with an audiologist to review the user experience and potentially make an adjustment or configuration for their hearing devices. Additionally, some prior devices require costly and inconvenient or obtrusive components, such as external microphones, for adjusting the sound experienced by a patient. Moreover, current devices essentially allow users to adjust volume and switch between a few preconfigured settings on their device.

In contrast, via use of principles of the present disclosure and exemplary systems and methods as disclosed herein, cochlear implants having improved performance and user experience may be realized. In one exemplary embodiment, a cochlear implant system comprises a class II medical device that utilizes a neural network and mobile device application to recognize unique audio environments and automatically and/or intelligently alter one or more settings of a patient's cochlear implants. In this manner, a user of an exemplary system is provided a level of control over their cochlear implant performance and settings that was typically only available to audiologists.

Exemplary embodiments implement a software platform for advanced filtering of sounds, both through pre-existing devices as well as custom hardware. Exemplary embodiments work in tandem with and/or utilize a custom mobile device application to give patients more control over what they hear through their cochlear implants without sacrificing the safety and accuracy of a traditional audiologist setup. In exemplary embodiments, user-feedback driven AI is utilized to achieve improved noise filtering and audio performance. The present disclosure and exemplary systems make it possible for several settings profiles to be stored that are optimized for specific environments. Further, the user not only has the ability to switch between them, but have this automated for them once an accuracy threshold is met by a scene recognition neural network. Additionally, the user has the ability to adjust these accuracy thresholds so that they can increase/ decrease the likelihood of a particular setting profile being employed. Yet further, in some embodiments the patient can customize a copy of the audiologists setting profile to their liking, but without having associated permissions necessary to overwrite the original settings. The patient also has the ability to make any of their customized audio settings mapped to any of the scenes recognized by the neural network so they can further customize behavior of an exemplary system. The present disclosure and exemplary systems aim to improve notable shortcomings of current cochlear devices, such as a lack of fine control over patient hearing, noise, and environmental versatility. Some embodiments utilize an enhanced user interface to display more control features to the user, and tie in an automatic scene-detection filter powered by a user-driven neural network algorithm.

Figure 1B:
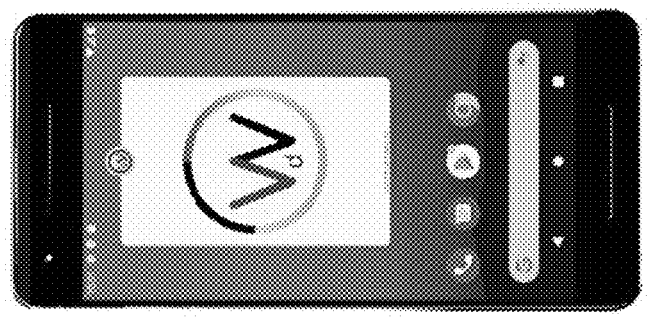
FIG. 1B illustrates an exemplary cochlear implant system, in accordance with various embodiments.
Figure 1B:
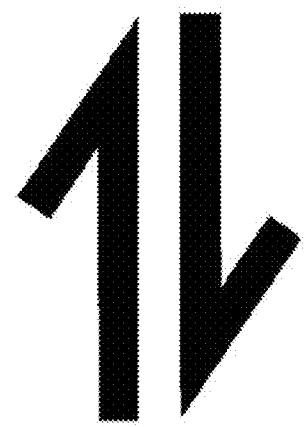
Figure 1B:
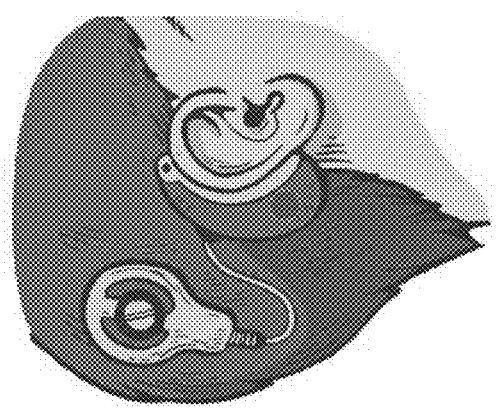
Figure 1B:
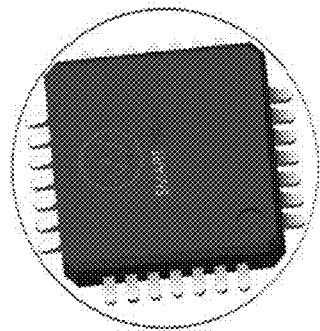

With reference to FIGS. 1A and 1B, in various exemplary embodiments, a cochlear implant system 100 comprises a control application 110 operative on a mobile device, a neural network 120, and a cochlear implant 130. Control application 110 is communicatively coupled to cochlear implant 130. Neural network 120 may be contained within control application 110 and/or otherwise operative on the mobile device; alternatively, neural network 120 may be remote from the mobile device while being communicatively accessible thereto. In various exemplary embodiments, cochlear implant system 100 comprises one or more of a Bluetooth capable cochlear implant 130, a smartphone or other mobile device having Bluetooth capabilities, and a software application configured to interact with cochlear implant 130 utilizing Bluetooth communication. In some embodiments, the software application utilizes the following rights or permissions on the mobile device: read/write permissions, audio recording, and Bluetooth interface. In some embodiments, cochlear implant system 100 utilizes signal processing and/or filtering hardware such as a dual programmable gain amplifier, operational amplifiers, and/or the like; in other embodiments, such hardware may be included in and/or form a part of cochlear implant 130. Moreover, it will be appreciated that in some embodiments, cochlear implant system 100 comprises solely a software application operative on a mobile device, the mobile device being capable of communication with a cochlear implant and with a data network such as the internet.

Via use of system 100, a user may achieve improved hearing results and/or audio performance. For example, system 100 may allow the user to non-destructively modify, change, and/or override presets for a cochlear implant (for example, presets selected by an audiologist of the user) in order to reduce and/or eliminate the perception of undesirable audio information (i.e., noise) arising from an ambient noise environment. In this manner, the user achieves more fine-grained control of performance, and eliminates the need to return to the audiologist for minor setting adjustments. Additionally, the user can maintain comfortable and effective hearing performance while moving among diverse audio environments.

Figure 2:
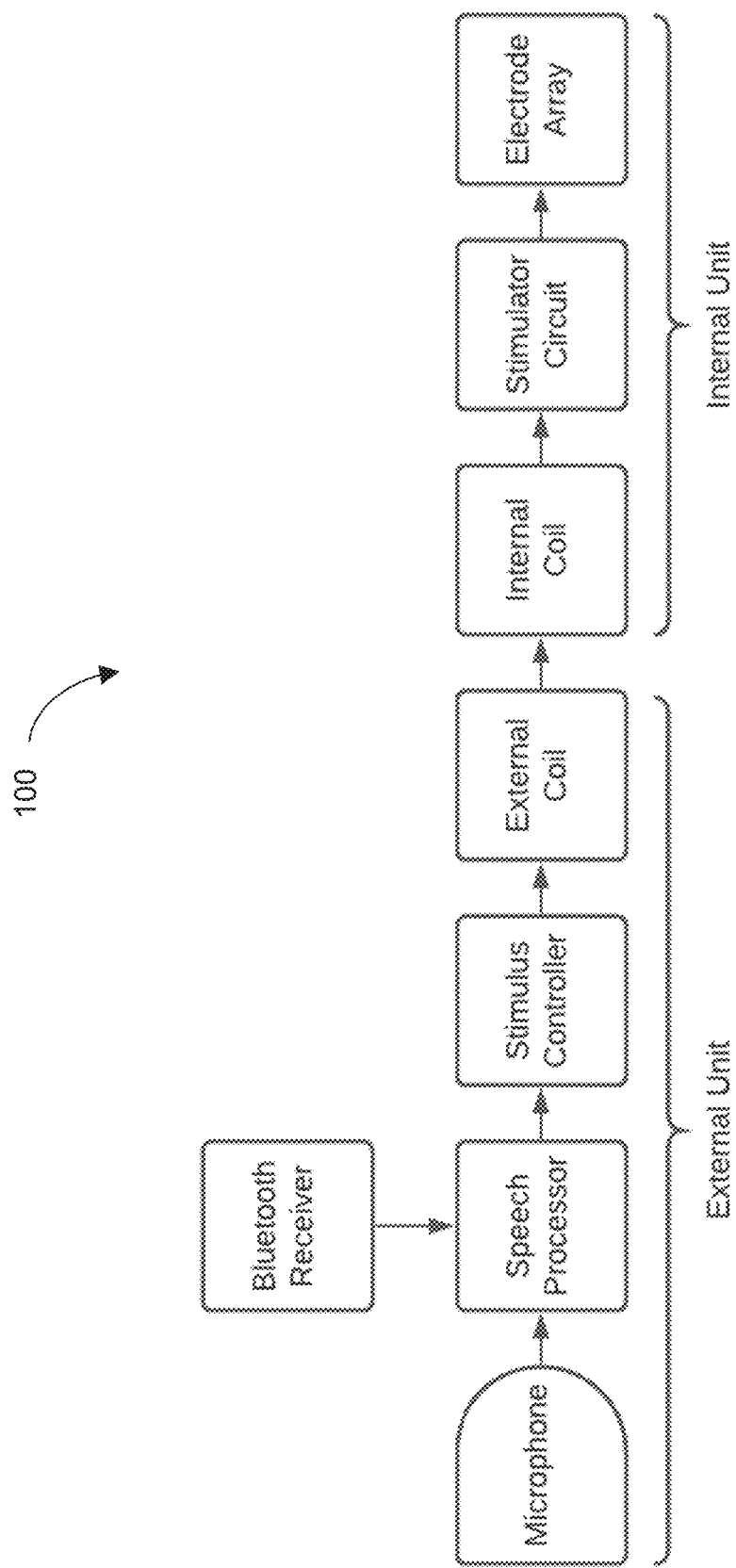
FIG. 2 illustrates a flowchart of components and operation of a cochlear implant system in accordance with various embodiments.

With reference now to FIG. 2, exemplary processing and/or filtering may be achieved in system 100 via use of a filter circuit, for example a filter circuit utilizing one or more programmable gain amplifiers (for example, model LTC6912HGN-2#PBF from Analog Devices, Inc., or similar), one or more operational amplifiers (for example, model LTC6242HGN#TRPBF from Analog Devices, Inc. or similar), resistors, capacitors, and/or inductors as suitable. Settings in the filter circuit may be adjusted, for example in order to provide a frequency response corresponding to a low-pass filter, a high-pass filter, a band-pass filter, a band-stop filter, or other desired frequency response. It will be appreciated that multiple filter stages may be utilized and/or that analog and/or digital filtering or DSP processing approaches may be utilized. For example, if system 100 determines that ambient noise is located primarily above 4400 Hz, system 100 may implement a low-pass filter function that attenuates audio information above this frequency. In another example, if system 100 determines that ambient noise is located primarily below 300 Hz, system 100 may implement a high-pass filter function that attenuates audio information below this frequency range. In still another example, if system 100 determines that ambient noise is located primarily in the 800 Hz to 920 Hz range, system 100 may implement a filter function that generally passes audio information falling below or above this range, while significantly attenuating audio information falling in this range (i.e., a band-stop filter). Moreover, system 100 may attenuate multiple frequency ranges, for example simultaneously attenuating audio information between 400 Hz and 440 Hz and between 3200 Hz and 3400 Hz, while generally passing audio information falling outside these frequency bands. As discussed herein, filter configuration may be implemented, controlled, and/or modified via operation of neural network 120.

With reference now to FIG. 3, an exemplary cochlear implant system 100 may utilize a defined set of noise environments and corresponding filtering settings, for example noise environments corresponding to 10 ambient environments found in an airport, bus, metro or subway, metro or subway station, park, public square, shopping mall, street with pedestrians, street with automobile traffic, and/or tram. However, any suitable number and/or configuration of noise environments and corresponding filtering settings may be utilized, as desired. Control application 110 obtains ambient audio information around the user, for example via the microphone of the mobile device, or alternatively via a microphone of a cochlear implant. Neural network 120 processes the ambient audio information and identifies a predicted class of noise environment (for example, when exemplary ambient audio information is obtained from a London park, it can be seen that system 100 predicts the ambient audio environment to be a "park" with very high certainty).

Moreover, system 100 may monitor and/or record audio information for a new environment, for example in response to a user activating a button in control application 110, The recorded audio information may be utilized to train neural network 120. In this manner, a user of system 100 is not limited to the preset audio environments and consequent improved filtering and audio performance associated therewith; rather, the user can "teach" system 100 to recognize additional audio environments and, via feedback, ratings, or other responses provided by the user via, control application 110, allow system 100 to learn how to optimally filter new environments and/or environments that significantly differ from set environments.

Moreover, control application 110 may utilize position or location information, for example UPS information obtained from the mobile device on which control application 110 is installed, in order to select and/or implement an update to cochlear implant 130. Time, traffic, or other information may also be utilized. For example, when position information shows the user is at a train station and time information shows that time is when the station is typically busy, that information may be utilized to fully or at least partially select (or influence the selection of) audio filter configuration of cochlear implant 130.

Yet further, position information may be utilized to trigger an ambient audio sampling. For example, a user passing into or out of a building may trigger an operation of control application 110 and a consequent potential update of settings of cochlear implant 130. Additionally, the ambient noise environment may be analyzed at a regular interval, for example every 5 seconds, every 10 seconds, every 30 seconds, every 1 minute, every 5 minutes, or the like, in order to provide a regularly updated configuration for cochlear implant 130.

Additionally, a user may trigger a potential update to settings for cochlear implant 130, for example by clicking a button in control application 110, for example clicking when, in the user's opinion, the current settings offer sub-optimal results and the user would like an updated assessment of the ambient noise environment to be performed.

In some exemplary embodiments, in operation of system 100, adjustments to settings of cochlear implant 130 may be persistent; stated another way, a change of settings may remain until a further change is instructed. In other exemplary embodiments, adjustments to settings of cochlear implant 130 may be temporary. For example, when control application 110 is minimized and/or closed, control application 110 may transmit an instruction to cochlear implant 130 to return to a default set of operating parameters, for example those selected or assigned by an audiologist of the user.

System 100 may be updated and/or upgraded, for example with updated class information for external noise environments stored in control application 110. Moreover, system 100 may provide audio information back to a central server or control system for use in refining external noise environment information or creating new external noise environment classes.

Additionally, system 100 may provide history information to a user's audiologist. The audiologist may review the operational history information and determine that revised default settings for cochlear implant 130 may be desirable; the updated settings can be transmitted back to control application 110 and thereafter sent to cochlear implant 130 for implementation.

With reference now to FIG. 3, in various exemplary embodiments neural network 120 comprises a neural network written in python using TensorFlow, TensorFlow neural networks were converted to TensorFlow Lite networks which could be utilized from within a variety of mobile applications. For testing purposes, the Android operating system was chosen to run a mobile application developed using Android Studio and written in Java. It is important to note that neural network 120 is not required to be implemented using these technologies/languages specifically, and that it would be suitable to implement with others such as PyTorch and C++.

Figure 4A:
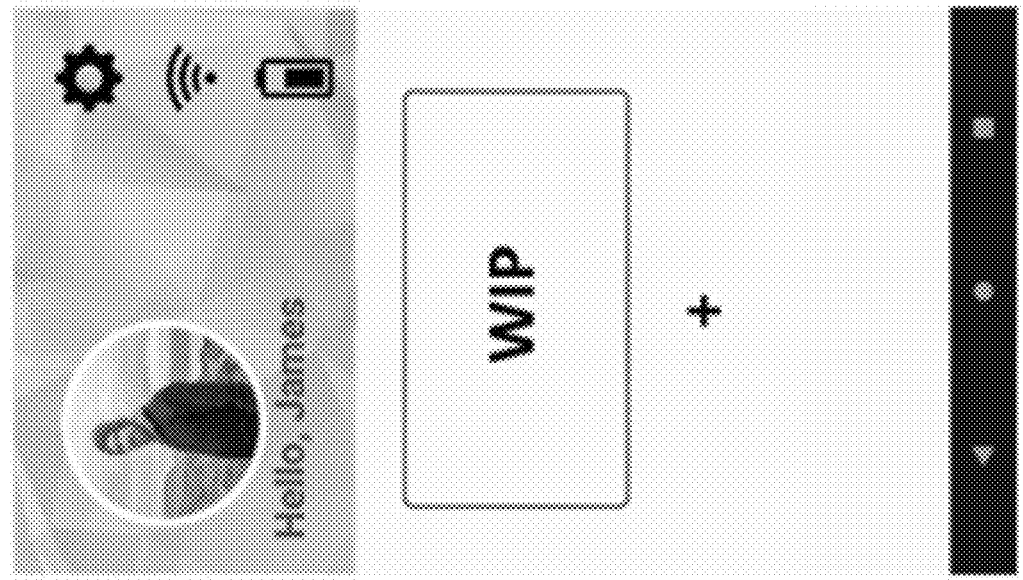
FIGS. 4A, 4B, and 4C illustrate operation of mobile application components of an exemplary cochlear implant system in accordance with various embodiments.
Figure 4A:
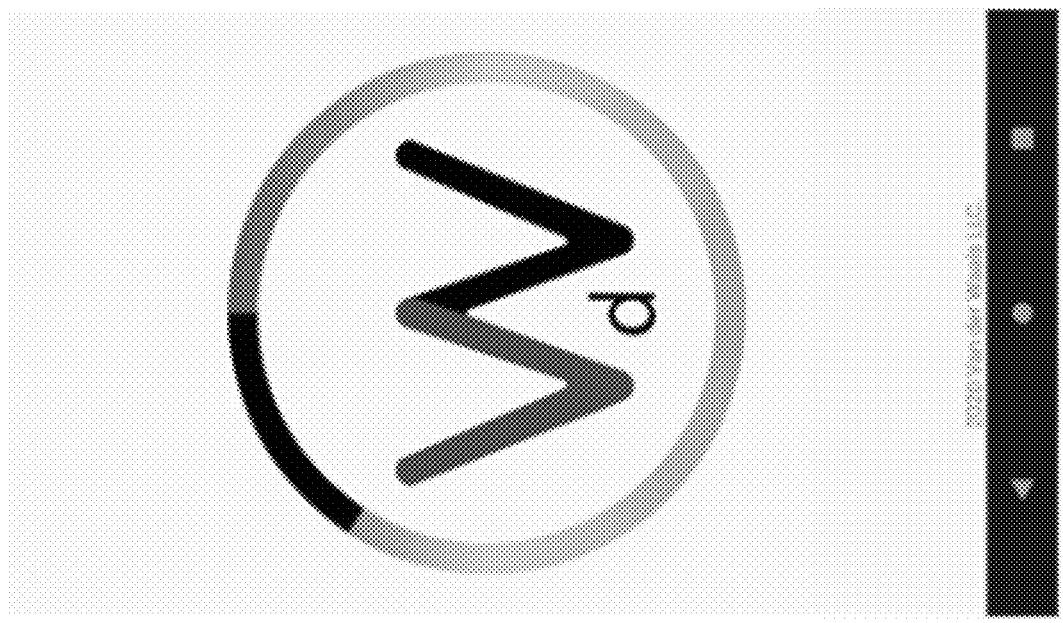
Figure 4B:
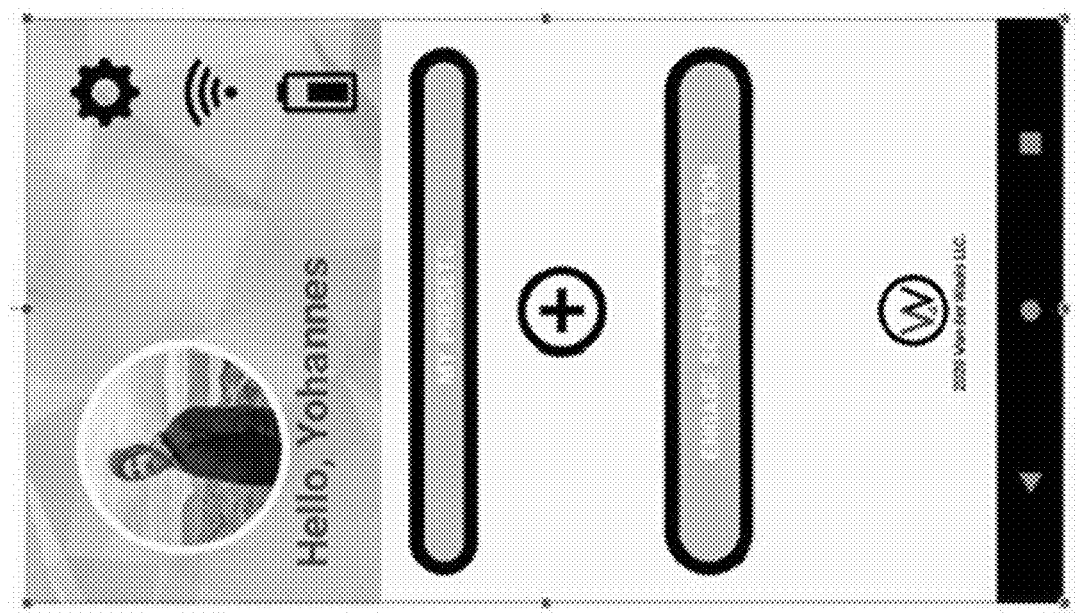
Figure 4B:
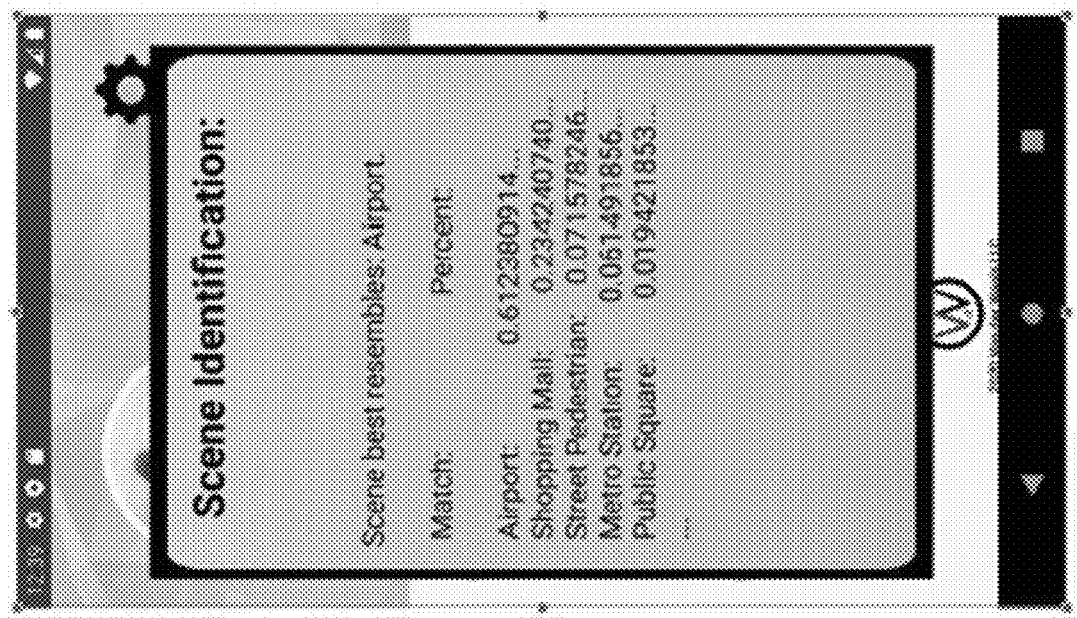
Figure 4C:

With reference now to FIGS. 4A, 4B, and 4C, in various exemplary embodiments control application 110 is utilized to process data through our complementary mobile application. Specifically, audio data may be recorded for small windows of time (for example, between about 30 seconds and about 60 seconds) and stored in temporary files within the file system. These raw audio files are converted to MFCCs within control application 110, which the neural network 120 has been trained to classify as specific audio environments. If a confidence threshold is reached in this classification, control application 110 will modify the user's settings determined by a trained audiologist ahead of time to optimally process sound within the specific environment. In some embodiments, another layer of learning is implemented within control application 110 that implements real time noise canceling separate from the scene classification performed by neural network 120. Moreover, certain exemplary embodiments employ federated learning such that weights within neural network 120 may continue to be updated, and benefit from the data processed in the broader network of patient applications accessible to control application 110. It will be appreciated that control application 110 is where neural network 120 data collection is processed/transferred, and where the user's interface for settings, account details, updates, and so forth are hosted and accessible.

Figure 5:
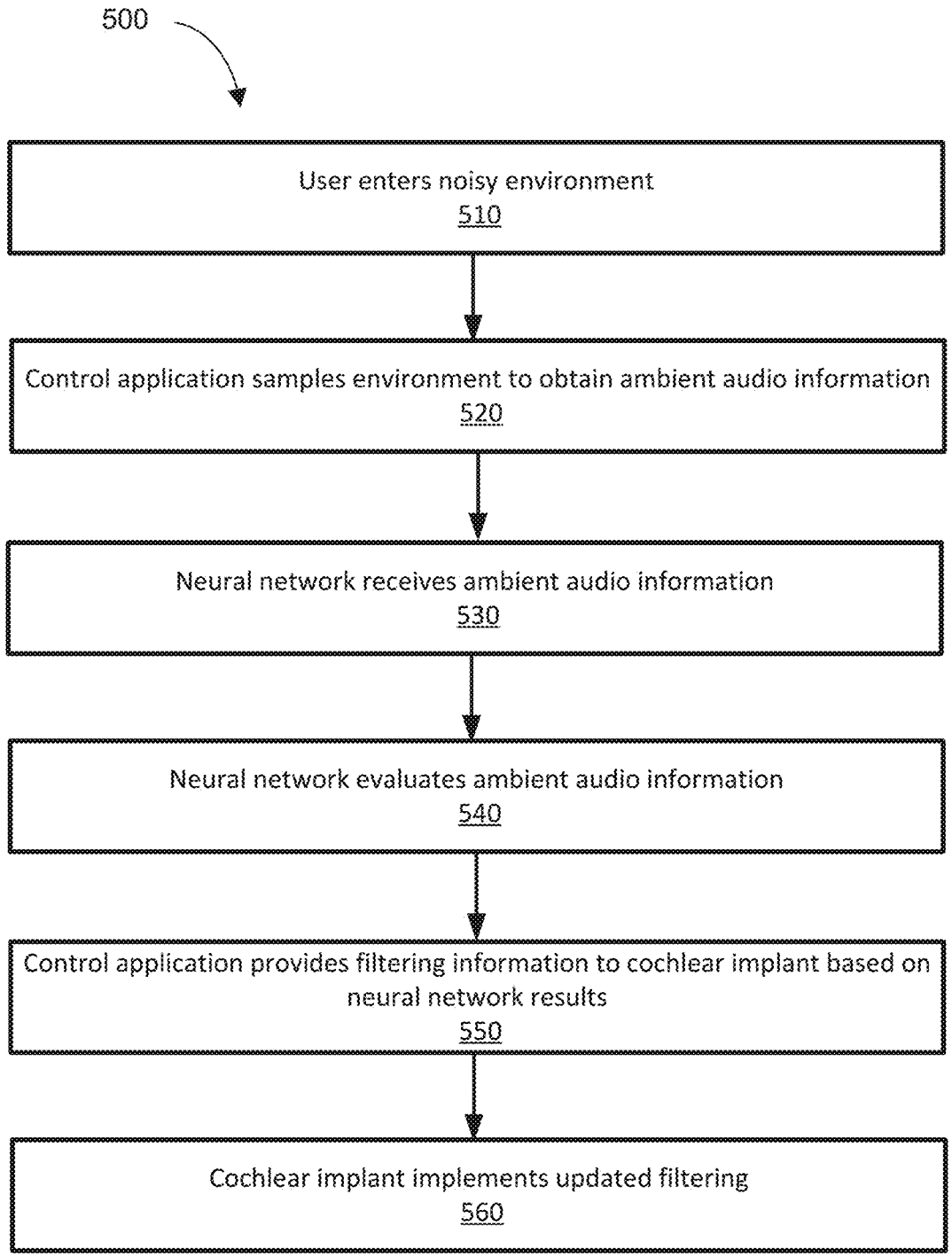
FIG. 5 illustrates a method of controlling a cochlear implant in accordance with various embodiments.

With reference now to FIG. 5, in an exemplary embodiment a method 500 for dynamic control of a cochlear implant is provided. A user may enter, approach, or otherwise draw near to or be surrounded by a noisy environment, such as a subway station (step 510). A control application operative on a smartphone or other mobile device of the user may sample, measure, or otherwise monitor or assess the ambient audio environment, for example utilizing a microphone of the mobile device. The ambient audio environment may be converted to and/or represented as a mel-frequency cepstrum (WC) comprising a set of mel-frequency cepstral coefficients (MFCCs) (step 520). The MFCCs are passed as inputs to a neural network, for example a neural network residing and/or operative: (i) in the control application 110, (ii) elsewhere on the mobile device, or (iii) remote from the mobile device but in electronic communication therewith (for example, in a cloud service (step 530). The neural network evaluates the MFCCs, and identifies (for example, among a set of pre-defined ambient noise environments based on prior sampling or pre-configured options) a predicted ambient noise environment (step 540). The control application communicates with the cochlear implants of the user (for example, via a wireless link between the cochlear implants and the mobile device) frequency filtering information based on the predicted ambient noise environment (step 550). The cochlear implants implement the updated frequency filtering information, resulting in improved audio performance for the user (for example, by reducing the level of "background" or "white" noise) (step 560), Via operation of method 500, a user is enabled to hear distinct sounds in their environment rather than jumbled white noise, without requiring any active steps of the user. Rather, method 500 may be operative on a triggered basis, an on-demand basis, a polled basis, an interrupt basis, or on any suitable timeline or reason in order to implement and maintain an optimized audio experience for the user, for example as the user moves between quiet and noisy locations and back again, or the like.

Exemplary methods and processes disclosed herein improve the functioning of a computer system. For example, exemplary principles enable improved battery life for a cochlear implant by applying improved filtering, allowing the user to operate the device at a lower volume level that requires a lower power draw. In this regard, by transmitting, storing, and/or accessing data using the processes described herein, the quality of the data is improved and errors are reduced. Such improvements also increase the efficiency of a network by reducing the portion of duplicated processes or redundant or inefficient calculations. In various embodiments, processing data based on the methods disclosed herein reduces back end processing and reduces processing time for data analysis, In this regard, the processes may save processing resources including CPU time, memory resources, and/or network or other communications resources.

System 100 may be computer based, and may comprise a processor, a tangible non-transitory computer-readable memory, and/or a network interface, along with other suitable system software and hardware components. Instructions stored on the tangible non-transitory memory may allow system 100 to perform various functions, as described herein. System 100 may comprise or utilize a network, computer-based system, and/or software components configured to implement the functions or capabilities of system 100. For example, a mobile device may comprise a smartphone, tablet, personal digital assistant, and/or the like. A cochlear implant may comprise various batteries, receivers/stimulators, transmitters, microphones, electrode arrays, and/or the like as is known in the art.

Moreover, it will be appreciated that, in addition to use in connection with cochlear implants, principles of the present disclosure may be applied to video conferencing applications, cellular communication applications, military communication applications, noise cancelling headphone applications, and/or the like.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "satisfy," "meet," "match," "associated with", or similar phrases may include an identical match, a partial match, meeting certain criteria, matching a subset of data, a correlation, satisfying certain criteria, a correspondence, an association, an algorithmic relationship, and/or the like. Similarly, as used herein, "authenticate" or similar terms may include an exact authentication, a partial authentication, authenticating a subset of data, a correspondence, satisfying certain criteria, an association, an algorithmic relationship, and/or the like.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in *In re Nuijten* to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure, The scope of the disclosure is accordingly limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. AU structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. § 112(f) unless the element is expressly recited using the phrase "means for" or "step for". As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

In various exemplary embodiments, computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks, These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program product and loaded into a computer system using a removable storage drive, hard disk drive, or communications interface. The control logic (software), when executed by the processor, causes the processor to perform functions of various embodiments as described herein. In various embodiments, hardware components may take the form of application specific integrated circuits (ASICs). Implementation of the hardware so as to perform the functions described herein will be apparent to persons skilled in the relevant art(s).

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: audio data; filter data; user data; and/or like data useful in the operation of an exemplary system. As those skilled in the art will appreciate, a user computer or mobile device may include an operating system as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments may be referred to in terms, such as matching, determining, or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning, AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In various embodiments, the embodiments are directed toward one or more computer systems capable of carrying out the functionalities described herein. The computer system includes one or more processors. The processor is connected to a communication infrastructure (e.g., a communications bus, cross-over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Moreover, any database may be organized in any suitable manner, for example, as data tables or lookup tables. Each record may be a single file, a series of files, a linked series of data fields, or any other data structure.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance, For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825; other proprietary techniques that may include fractal compression methods, image compression methods, and the like.

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not for purposes of limitation. For example, the steps recited in any of the method or process descriptions may be executed in any order and are not limited to the order presented. Moreover, any of the functions or steps may be outsourced to or performed by one or more third parties. Modifications, additions, or omissions may be made to the systems, apparatuses, and methods described herein without departing from the scope of the disclosure. For example, the components of the systems and apparatuses may be integrated or separated. Moreover, the operations of the exemplary systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. Furthermore, any reference to singular includes plural embodiments, and any reference to more than one component may include a singular embodiment. Although specific advantages have been enumerated herein, various embodiments may include some, none, or all of the enumerated advantages.

What is claimed is:

1. A computer-based method for controlling a cochlear implant, the method comprising:
    sampling, by a mobile application operative on a mobile device, an audio environment around a user of the cochlear implant to obtain audio environment information;
    converting the audio environment information to a set of mel-frequency cepstral coefficients;
    processing, by a neural network, the set of mel-frequency cepstral coefficients to determine a level of matching against a set of pre-defined noise environments;
    based on the level of matching, selecting, by the mobile application, filter configuration information associated with the best match in the set of pre-defined noise environments;
    transmitting, by the mobile application and over a wireless link to the cochlear implant, the filter configuration information; and
    receiving, over a mobile network and by the mobile application, updated information comprising the set of pre-defined noise environments.

2. The method of claim 1, further comprising updating, by the cochlear implant and responsive to the filter configuration information, audio filter operation of the cochlear implant.

3. The method of claim 2, wherein the sampling is triggered by the user via an input to the mobile application.

4. The method of claim 1, wherein the sampling is triggered by a level of ambient noise detected by the control algorithm exceeding a pre-set decibel threshold.

5. The method of claim 1, wherein the mobile device is coupled to the cochlear implant via Bluetooth.

6. The method of claim 1, wherein the filter configuration information comprises instructions to implement at least one of a lowpass filter, a highpass filter, a bandpass filter, or a band-stop filter.

7. The method of claim 1, further comprising transmitting, by the mobile application and over a wireless link to the cochlear implant, an instruction for the cochlear implement to return to a default filter configuration selected by an audiologist of the user.

8. The method of claim 7, wherein the instruction is transmitted responsive to the user closing the mobile application.

9. The method of claim 1, further comprising:
    storing, in the mobile application, history information for changes to the filter configuration of the cochlear implant; and
    transmitting, by the mobile application and responsive to a signal from a user, the history information to an audiologist of the user.

10. The method of claim 9, further comprising:
    receiving, from the audiologist and responsive to the history information, updated default configuration information for the cochlear implant; and
    transmitting, by the mobile application and to the cochlear implant, the updated default configuration information.

11. A computer-based method for controlling a cochlear implant, the method comprising:
    sampling, by a mobile application operative on a mobile device, an audio environment around a user of the cochlear implant to obtain audio environment information;
    converting the audio environment information to a set of mel-frequency cepstral coefficients;
    processing, by a neural network, the set of mel-frequency cepstral coefficients to determine a level of matching against a set of pre-defined noise environments;
    based on the level of matching, selecting, by the mobile application, filter configuration information associated with the best match in the set of pre-defined noise environments; and
    transmitting, by the mobile application and over a wireless link to the cochlear implant, the filter configuration information,
    wherein the neural network utilizes federated learning to revise one or more weights in the neural network.

12. A computer-based method for controlling a cochlear implant, the method comprising:
    sampling, by a mobile application operative on a mobile device, an audio environment around a user of the cochlear implant to obtain audio environment information;
    converting the audio environment information to a set of mel-frequency cepstral coefficients;
    processing, by a neural network, the set of mel-frequency cepstral coefficients to determine a level of matching against a set of pre-defined noise environments;
    based on the level of matching, selecting, by the mobile application, filter configuration information associated with the best match in the set of pre-defined noise environments;
    transmitting, by the mobile application and over a wireless link to the cochlear implant, the filter configuration information; and
    transmitting, over a mobile network and by the mobile application, the audio environment information to a central server for use in creating a new pre-defined noise environment to be included in the set of predefined noise environments.

\* \* \* \* \*